(12) United States Patent
Cook

(10) Patent No.: US 12,343,516 B2
(45) Date of Patent: Jul. 1, 2025

(54) INTRACARDIAC PERCUTANEOUS PUMP FOR CIRCULATORY SUPPORT AND RELATED SYSTEMS AND METHODS

(71) Applicant: Venstramedical Pty Limited, Bar Beach (AU)

(72) Inventor: Martin Cook, Eden Prairie, MN (US)

(73) Assignee: Venstramedical Pty Limited, Eden Prairie, MN (US)

( * ) Notice: Subject to any disclaimer, the term of this patent is extended or adjusted under 35 U.S.C. 154(b) by 860 days.

(21) Appl. No.: 17/251,619

(22) PCT Filed: Jun. 6, 2019

(86) PCT No.: PCT/IB2019/054699
§ 371 (c)(1),
(2) Date: Dec. 11, 2020

(87) PCT Pub. No.: WO2019/239259
PCT Pub. Date: Dec. 19, 2019

(65) Prior Publication Data
US 2021/0220634 A1 Jul. 22, 2021

Related U.S. Application Data

(60) Provisional application No. 62/683,819, filed on Jun. 12, 2018.

(51) Int. Cl.
*A61M 60/139* (2021.01)
*A61M 60/148* (2021.01)
(Continued)

(52) U.S. Cl.
CPC ........ *A61M 60/139* (2021.01); *A61M 60/148* (2021.01); *A61M 60/178* (2021.01);
(Continued)

(58) Field of Classification Search
CPC .. A61M 60/861; A61M 60/135; A61M 25/01; A61M 25/04; A61M 60/205;
(Continued)

(56) References Cited

U.S. PATENT DOCUMENTS 6,136,025 A * 10/2000 Barbut ................ A61M 60/867
623/3.15
6,217,541 B1 4/2001 Yu
(Continued)

FOREIGN PATENT DOCUMENTS

WO 2010133567 11/2010
WO 2019239259 12/2019

OTHER PUBLICATIONS

"International Application Serial No. PCT IB2019 054699, International Search Report mailed Aug. 23, 2019", 11 pgs.
(Continued)

*Primary Examiner* — Mark W. Bockelman
(74) *Attorney, Agent, or Firm* — SCHWEGMAN LUNDBERG & WOESSNER, P.A.

(57) ABSTRACT

A device comprises an implantable blood pump receivable in a sheath for percutaneous delivery. The implantable blood pump comprises a collapsible impeller mounted in a collapsible impeller cage, and a drive device mounted in a housing. The housing is in connection between a first end of a catheter and the collapsible impeller cage. The drive device is adapted for rotating the collapsible impeller. A retractable support structure is adapted to extend from the catheter. The extended retractable support structure is adapted to engage with the wall of the aorta for allowing the implantable blood pump to be secured in the left ventricle. The collapsible impeller cage comprises an inlet and an
(Continued)

outlet. The inlet is adapted to receive blood from the left ventricle. The outlet directs blood in the direction of the atrioventricular valve.

17 Claims, 11 Drawing Sheets

(51) Int. Cl.
*A61M 60/178* (2021.01)
*A61M 60/216* (2021.01)
*A61M 60/237* (2021.01)
*A61M 60/414* (2021.01)
*A61M 60/419* (2021.01)
*A61M 60/808* (2021.01)
*A61M 60/81* (2021.01)

(52) U.S. Cl.
CPC ........ *A61M 60/216* (2021.01); *A61M 60/237* (2021.01); *A61M 60/414* (2021.01); *A61M 60/419* (2021.01); *A61M 60/808* (2021.01); *A61M 60/81* (2021.01); *A61M 2205/0266* (2013.01); *A61M 2205/103* (2013.01); *A61M 2210/125* (2013.01); *A61M 2210/127* (2013.01)

(58) Field of Classification Search
CPC .............. A61M 60/50; A61M 2206/20; A61M 60/139; A61M 60/148; A61M 60/178; A61M 60/216; A61M 60/237; A61M 60/414; A61M 60/419; A61M 60/808; A61M 60/81; A61M 2205/0266; A61M 2205/103; A61M 2210/125; A61M 2210/127; A61M 60/13
See application file for complete search history.

(56) References Cited

U.S. PATENT DOCUMENTS

| | | | |
|---|---|---|---|
| 6,544,216 | B1 | 4/2003 | Sammler et al. |
| 8,690,749 | B1 | 4/2014 | Nunez |
| 10,662,967 | B2 | 5/2020 | Scheckel |
| 11,219,755 | B2 * | 1/2022 | Siess .................... A61M 60/216 |
| 11,511,103 | B2 * | 11/2022 | Salahieh ............. A61M 60/221 |
| 11,839,753 | B2 | 12/2023 | Van Horne |
| 2008/0132747 | A1 | 6/2008 | Shifflette |
| 2011/0196190 | A1 | 8/2011 | Farnan et al. |
| 2016/0000983 | A1 * | 1/2016 | Mohl ................... A61M 60/17 600/16 |
| 2016/0089482 | A1 * | 3/2016 | Siegenthaler ....... A61M 60/419 600/16 |
| 2017/0290965 | A1 | 10/2017 | Mcbride et al. |
| 2017/0340791 | A1 | 11/2017 | Aboul-hosn et al. |
| 2021/0162196 | A1 | 6/2021 | Georges et al. |
| 2021/0268264 | A1 | 9/2021 | Stotz et al. |
| 2022/0080185 | A1 | 3/2022 | Clifton et al. |
| 2022/0105337 | A1 | 4/2022 | Salahieh et al. |

OTHER PUBLICATIONS

"International Application Serial No. PCT IB2019 054699, Written Opinion mailed Aug. 23, 2019", 9 pgs.

"International Application Serial No. PCT IB2019 054699, International Preliminary Report on Patentability mailed Dec. 24, 2020", 11 pgs.

Hsu, Po-Lin, "Review of Recent Patents on Foldable Ventricular Assist Devices", Recent Patents on Biomedical Engineering, 2012, vol. 5, 15pgs., (Jun. 2012), 15 pgs.

* cited by examiner

INTRACARDIAC PERCUTANEOUS PUMP FOR CIRCULATORY SUPPORT AND RELATED SYSTEMS AND METHODS

BACKGROUND OF THE INVENTION

Field of the Invention

The present invention relates to mechanical circulatory support methods, devices, and systems for supporting weakened and/or ailing hearts and more specifically to such devices, systems, and methods for providing short term support via a percutaneous catheter delivered pump.

Description of the Related Art

Mechanical circulatory support has become a standard of practice for the treatment of late-stage heart failure. The most common method of providing mechanical circulatory support is a left ventricular assist device ("LVAD"), which is a pump that takes over much of, if not all, the function of the left ventricle. LVADs are larger devices that may be placed via a surgical implantation technique for chronic support. In contrast, an intracardiac blood pump is a smaller device that can be implanted into the heart without major surgery via a catheter delivered through the arterial/venous system. Such devices are often called 'percutaneous pumps' or 'catheter pumps'.

Percutaneous pump housings must have a relatively small diameter to allow for positioning via the vascular system of the patient and are typically less than about 7 mm in diameter. Percutaneous pumps designed to support a failing left ventricle generally provide a blood flow output of about 4.5 L/min against 60-80 mmHg pressure, although lower flows may be acceptable for partial support.

Percutaneous pumps are usually designed to be placed or positioned during use such that they are disposed within or across the aortic valve as shown in FIG. 1. This arrangement has a number of disadvantages. The pump housing is typically a rigid, larger diameter body that can cause damage to the aortic valve leaflets due to contact with the large diameter and rigid housing. Placement of the housing such that it is disposed across the aortic valve may also place bending stress on the housing that may lead to structural failures or require more substantial structural design and larger devices. Forcing the flow through the housing may also provide resistance to the flow that is not trivial and requires a more powerful pumping mechanism and larger overall device. Additionally, positioning the housing through the aortic valve can result in a path for regurgitant flow back towards the ventricle in the event of a pump stoppage.

The pumping mechanism is typically in the form of a miniature axial flow rotary mechanism involving a rotating impeller disposed within the housing.

The above discussion relates primarily to placement of the pump housing such that it is positioned within or across the aortic valve during use but could equally apply to placement of such a housing such that it is positioned within or across the pulmonary valve or any other cardiac valve.

There is a need in the art for an improved intracardiac percutaneous pump and related systems and methods.

U.S. Pat. No. 5,169,378 describes an intraventricular expansible assist pump for use as circulatory support in patients with a severe ventricular cardiac shock. A disadvantage with this previous pump may be that the transvalvular segment which runs through the aortic valve expels blood in the aorta which may create a pressure difference between the aorta and the left ventricle such that the valve remains closed during the cardiac cycle due to the pressure difference when the device is in use.

EP Patent No. 0961621 and EP Patent No. 0925080 describe an intravascular blood pump which can be passed through the vasculature of the human body, for example to perform in the heart pumping action. These devices also pump blood into the aorta directly from a segment located in the aorta and may also create the pressure difference between the aorta and the left ventricle which may close the valve during the cardiac cycle when the device is in use.

U.S. Pat. No. 6,176,822 describes an intracardiac blood pump that it delivers blood from the left ventricle into the aorta. Similarly, this pump also expels blood in the aorta directly and also requiring the use of pressure sensors. This pump has an internal motor and a motor housing such that the internal motor in operation will generate heat to the motor surface which may be a significantly higher temperature than the physiological blood temperature. As blood flows along the motor surface, a possible disadvantage is that the expelled blood from the pump may be used to provide cooling to the hotter motor surface.

Any discussion of the prior art throughout the specification should in no way be considered as an admission that such prior art is widely known or forms part of common general knowledge in the field.

BRIEF SUMMARY OF THE INVENTION

Problems to be Solved

It may be advantageous to provide a device for assisting blood flow from the left ventricle to the aorta of the heart with the blood being expelled from the device at the left ventricle in the direction of the atrioventricular valve.

It may be an advantage to reduce or eliminate damage of the valve leaflets as a result of using a catheter with a much smaller diameter in comparison to a catheter with a pump housing.

It may be an advantage to ensure that the valve remains substantially competent from using the device.

It may be an advantage to reduce the risk of regurgitant flow in the event that the pump may stop for any reason.

It may be an advantage to eliminate the risk of physical stresses placed on the pump housing as a result of contact with the aorta or the valve.

It may be an advantage to allow for the impeller to be of a larger diameter than the catheter thus allowing for a reduced rotational speed which may reduce the likelihood of damage to the blood and may reduce loads on the mechanical drive system.

It may be an advantage to provide a device with a flow straightener such that the expelled blood is directed accurately in the direction of the atrioventricular valve.

It may be an advantage to provide a device operable with a motor external of the body to allow easy control and keep the diameter size of the device as low as possible.

It may be an advantage to provide a device with a Coanda surface such that the expelled blood travels along the outer surface of the device which also assists the direction of the blood flow to the aorta.

It may be an advantage to provide a retractable support structure which may be adapted to engage with the wall of the aorta for allowing the implantable blood pump to be secured in the left ventricle.

It may be an advantage to provide a device with a collapsible impeller and a collapsible impeller cage to keep the size the device as small as possible and also reducing the risk of snagging when inserting and moving the device through the tortuous anatomy of the heart to the desired location. Collapsible configuration of the pump and impeller allows for easier insertion or implantation of the device via the femoral artery reducing the need for sternomy.

It may be advantage to provide the collapsible impeller and a collapsible impeller cage with a shape memory metal so that it retains its functional shape to operate when the impeller and the impeller cage are expanded at the desired location.

It may be advantage to provide a device with a heat sink to dissipate the heat generated from moving parts of the device so that blood may not be heated as the blood contacts the outer surface of the device.

It is an object of the present invention to overcome or ameliorate at least one of the disadvantages of the prior art, or to provide a useful alternative.

Means for Solving the Problem

A first aspect of the present invention may relate a device adapted for use in assisting blood flow from the left ventricle to the aorta of the heart, the device may comprise: an implantable blood pump received in a catheter at a first end; the implantable blood pump may comprise a collapsible impeller mounted in a collapsible impeller cage, and a drive means mounted in a housing, wherein the housing may be in connection between the first end of the catheter and the collapsible impeller cage, wherein the drive means may be adapted for rotating the collapsible impeller; a retractable support structure adapted to extend from the catheter, wherein the extended retractable support structure may be adapted to engage with the wall of the aorta for allowing the implantable blood pump to be secured in the left ventricle; the collapsible impeller cage may comprise an inlet and an outlet, wherein the inlet may be adapted to receiving blood from the left ventricle, and wherein the outlet may direct blood in the direction of the atrioventricular valve.

Preferably, the retractable support structure may be at least one selected from the group of: a triangular stent-like structure, a rounded stent-like structure, a strut with barbs structure, and an expanded mesh.

Preferably, the implantable blood pump may be adapted to be extendable along the longitudinal axis of the catheter away from the first end of the catheter.

Preferably, the housing may comprise an outer Coanda surface adjacent to the outlet of the collapsible impeller cage such that blood may be directed along the outer Coanda surface.

Preferably, the collapsible impeller may be expandable, wherein the collapsible impeller may comprise a first metal and a first membrane, the first membrane may be in connection with the first metal, wherein the first metal may define the blade frame of the collapsible impeller, and wherein the first membrane may define the blade body of the collapsible impeller.

Preferably, the collapsible impeller cage may be expandable, wherein the collapsible impeller cage may comprise a second metal and a second membrane, the second membrane may be in connection with the second metal, wherein the second metal may define the frame of the collapsible impeller cage, and wherein the second membrane may define the body of the collapsible impeller cage.

Preferably, the first metal may be a first shape-memory alloy, and the second metal may be a second shape-memory alloy.

Preferably, the first membrane and the second membrane may be a polymer.

Preferably, the housing may comprise a heat sink. Preferably, the heat sink may also be encapsulated with in the lead or catheter body.

Preferably, the collapsible impeller may comprise a head portion and a tail portion, wherein the angle of attack may be proximal to the head portion.

Preferably, the inlet may comprise a plurality of inlet apertures, wherein the plurality of inlet apertures may be located between a distal end of the collapsible impeller cage and the head portion of the collapsible impeller.

Preferably, the outlet may comprise a plurality of outlet apertures, wherein each of the outlet apertures may be relatively equidistant from each other.

Preferably, the device may further comprise a first magnet mounted on an external motor, wherein the external motor may be adapted to provide rotational torque to a second magnet mounted on the drive means via magnetic coupling.

Preferably, the drive means may be a drive shaft, in which the drive shaft may be drive cable or a torque cable.

Preferably, the drive means may comprise an internal motor connected to a drive shaft, wherein the drive shaft may be attached to the collapsible impeller, wherein the internal motor may be adapted to provide rotational torque to the collapsible impeller.

Preferably, the motor may be a micromotor.

Preferably, the first metal and second metal may be flexible.

Preferably, the first membrane and the second membrane may be flexible.

A second aspect of the present invention may relate a pump assembly, comprising: an elongate catheter body; and a pump housing disposed at or near a distal end of the elongate catheter body, the pump housing comprising: a pump mechanism disposed within an interior of the pump housing; an inlet opening defined in a distal end of the pump housing, wherein the inlet opening may be in fluid communication with the interior; and an outlet opening may be defined in a proximal end of the pump housing, wherein the outlet opening may be in fluid communication with the interior of the pump housing.

Preferably, the pump housing may be configured to be positioned entirely within a ventricle during operation.

A third aspect of the present invention may relate to a method of pumping blood from a ventricle through an aortic valve, the method comprising: inserting a blood pump assembly through a blood vessel toward a heart, the blood pump assembly comprising: (a) an elongate catheter body; and (b) a pump housing disposed at or near a distal end of the elongate catheter body, the pump housing comprising: (i) a pump mechanism disposed within an interior of the pump housing; (ii) an inlet opening defined in a distal end of the pump housing, wherein the inlet opening is in fluid communication with the interior; and (iii) an outlet opening defined in a proximal end of the pump housing, wherein the outlet opening is in fluid communication with the interior; and positioning the blood pump assembly such that the catheter is disposed through the aortic valve and the pump housing is disposed entirely within the ventricle adjacent to the aorta valve.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

DETAILED DESCRIPTION OF THE INVENTION

Preferred embodiments of the invention will now be described with reference to the accompanying drawings and non-limiting examples.

The various embodiments disclosed or contemplated herein relate to a percutaneous pump that is designed to be placed within a cardiac chamber such that the pump housing is disposed within the chamber (rather than in or through the valve). As such, the inlet to the pump is within the chamber and the outlet is also within the chamber but placed close to the valve and directed to provide a stream of blood at the valve. In certain embodiments, the pump is an axial flow rotary pump.

In one embodiment, the pump is implanted via a transcatheter technique and the pump housing 10 is located at the tip of the catheter. That is, the pump housing 10, according to certain embodiments, is either coupled or attached to the distal end of the catheter or is integral with the distal end of the catheter.

Figure 1:
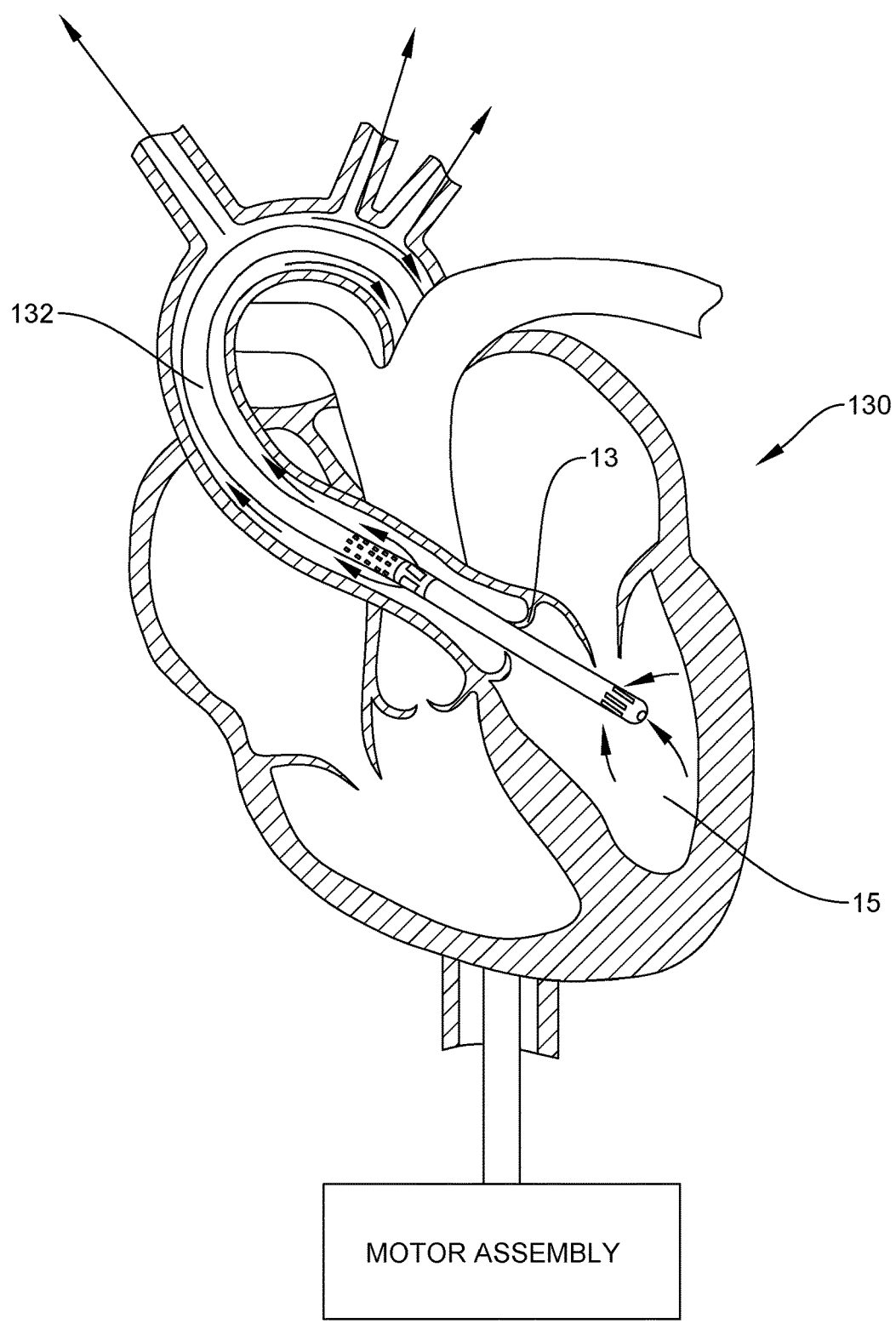
FIG. 1 is a view of a typical percutaneous blood pump placed across the aortic valve. (from prior art U.S. Pat. No. 9,907,890B2).
Figure 2:
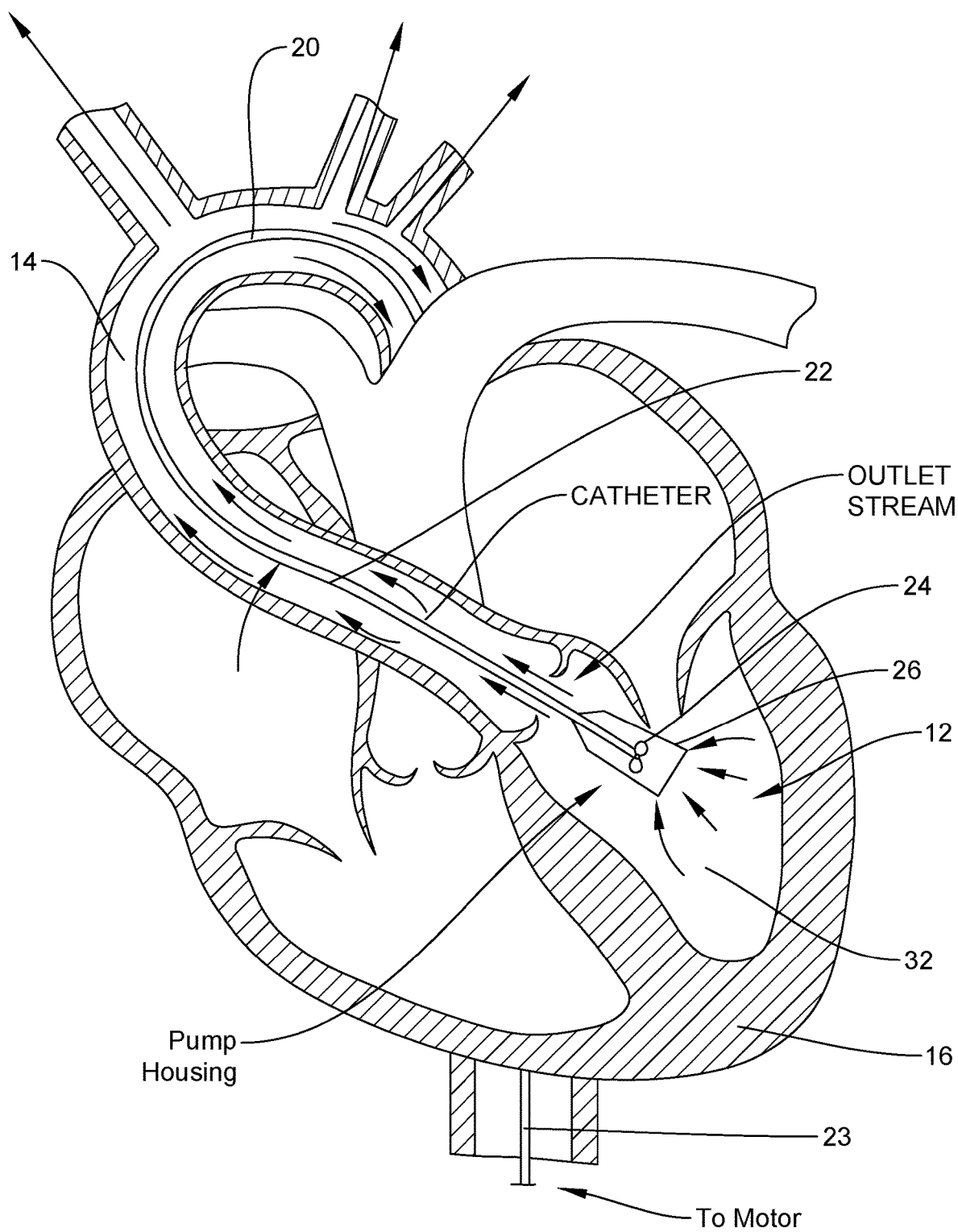
FIG. 2 is a cross-sectional schematic view of the intracardiac pump housing placed within the left ventricle adjacent to the aortic valve and the outflow stream of blood directed at the aortic valve.

In use, the catheter with the pump housing is inserted through a blood vessel such as the femoral artery of subclavian artery, for example, and the catheter is urged distally until the pump housing passes through the aortic valve and is disposed entirely within the ventricle, as shown in FIG. 2. Unlike known pumps as discussed above, no part of the pump housing or flow conduit is disposed within or across the aortic valve once the catheter and pump housing are positioned as desired. Instead, once the catheter and pump housing are in position, only the catheter, which is of relatively small diameter, is disposed within or across the aortic valve.

The advantages of positioning the pump housing in the ventricle such that only the catheter is disposed through the valve include, among others, (1) reducing or eliminating damage of the valve leaflets as a result of solely the catheter (with a much smaller diameter in comparison to the pump housing) being disposed therethrough, (2) ensuring that the valve remains substantially competent, (3) reducing the risk of regurgitant flow in the event that the pump stops for any reason, and (4) eliminating the risk of physical stresses placed on the pump housing as a result of contact with the aorta or the valve (5) Allows for the impeller to be of a larger diameter thus allowing for a reduced rotational speed which may reduce the likelihood of damage to the blood (haemolysis) and reduce loads on the mechanical drive system. The impeller rotational speed would be approximately 14,000 rpm but could be in the range 10,000-20,000 rpm.

Once the catheter and pump housing are positioned as depicted in FIG. 2, a stream of blood is ejected from the pump housing as shown (identified as "outlet stream"), either continuously or pulsatile, and opens the aortic valve due to the dynamic pressure of the stream. By placing the pump housing at the distal end of the catheter, the outlet of the pump housing will naturally align with the aortic valve and ensure that the pump output is directed into the aorta.

In another similar embodiment the outlet end of the pump may be placed such that it is adjacent to the Aortic valve leaflets but does not prevent their function. In this embodiment the pump position may be maintained by positioning the outlet 'snugly' into the Basal Ring. In this embodiment the support structures would project from near the outlet end of the pump to engage with the base of the ventricular aortic junction. The outlet of the pump may, in this embodiment be adjacent to the leaflets which may even contact the pump outlet when the leaflets are in the 'closed' configuration. However, the pump would not prevent the leaflets acting to prohibit retrograde flow back into the ventricle.

It is understood that the impeller within the pump housing is provided with torque via a cable (or shaft) (not shown) that runs through the catheter that is disposed through the aortic valve in certain embodiments. In these implementations, the torque generation unit is placed outside the body, but alternatively may be a small motor placed on the catheter within the aorta.

The pump (impeller and housing) may be rigid, or in another embodiment, can be collapsible from a compressed configuration, for implantation, to an expanded configuration once deployed.

Figure 4:
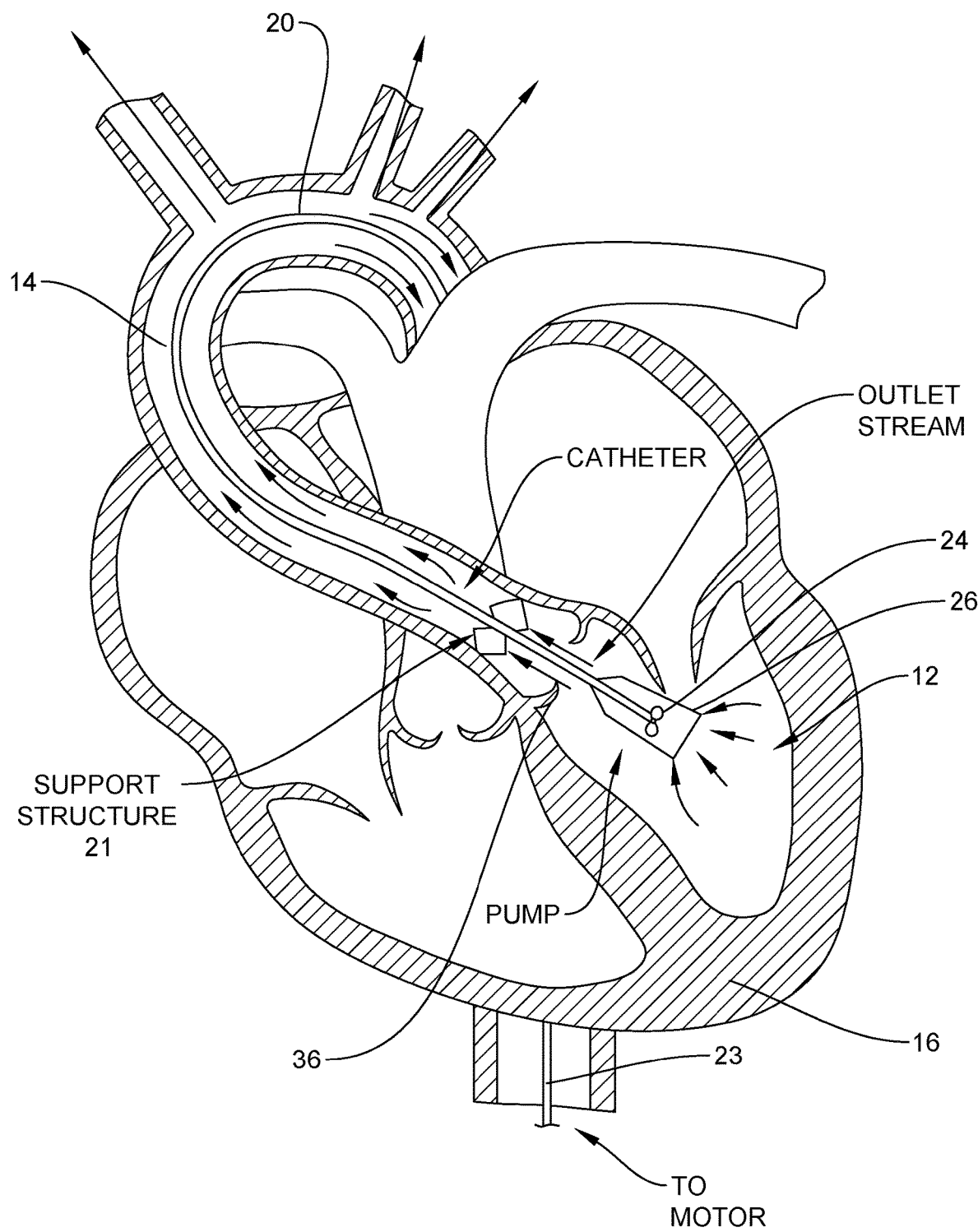
FIG. 4. is a cross-sectional schematic view of the support structure in the form of triangular stent-like structure.
Figure 5:
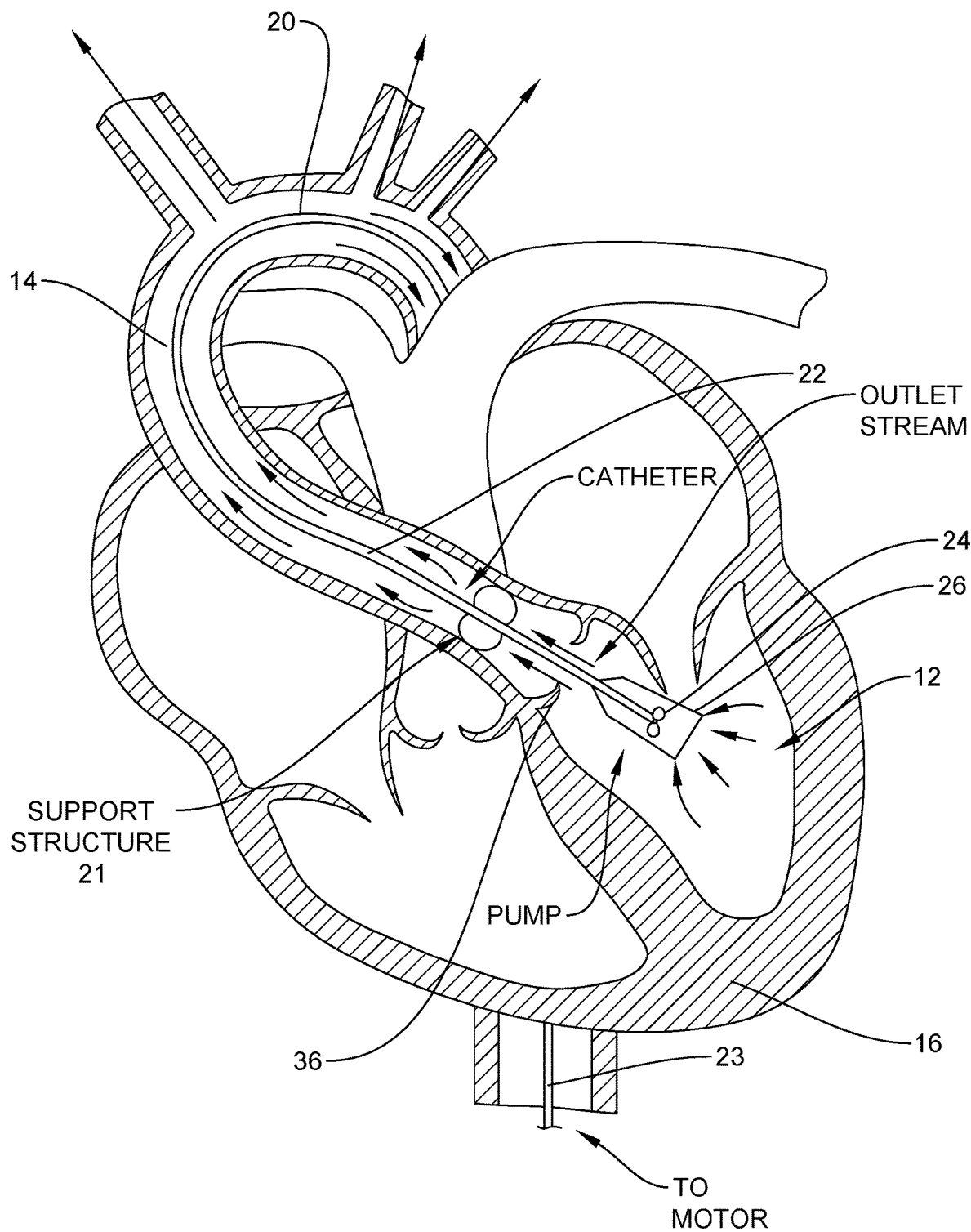
FIG. 5. is a cross-sectional schematic view of the support structure in the form of rounded stent-like structure.
Figure 6:
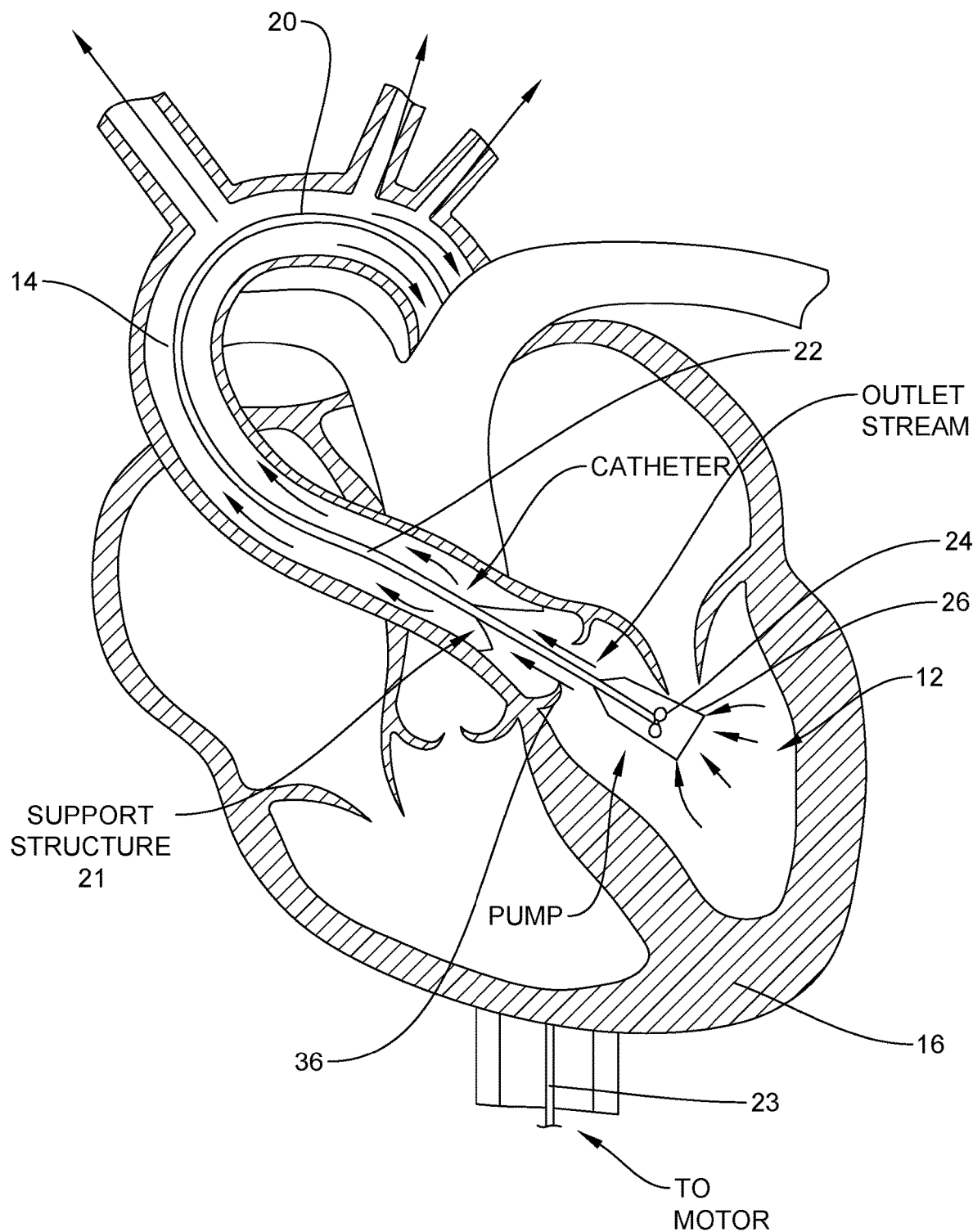
FIG. 6. is a cross-sectional schematic view of the support structure in the form of struts with barbs at their tips to engage the aortic wall.

As shown in FIGS. 4-6, according to certain embodiments, the pump assembly, including the catheter and the pump housing, is supported and maintained in position via a support structure that protrudes from the catheter while disposed in the aorta such that the support structure contacts the inner wall of the aorta. The support structure 21 can be a stent-like component, struts with or without barbs, a frame-like structure, or any other known structure or feature for providing support between a catheter and the inner wall of the vessel in which the catheter is disposed. The support structure would be collapsible from a small diameter configuration for implantation and extended once deployed to contact the aortic wall. In one embodiment, the support structure would be made of nitinol and expand once the delivery sheath was retracted allowing the support structure to expand.

The support structures may be in the form of a frame with a membrane covering and this membrane covering would allow for the support structures to also act as flow straighteners. Flow straighteners are a common feature of axial pumps that convert rotational energy of the fluid, induced into the flow by the rotating impeller of the pump, into pressure energy and assist in increasing the efficiency and overall performance of the pump. The frame members may be constructed of nitinol super elastic wire (or other suitable material) and the membrane may be of polyurethane or other haemocompatible material.

In various embodiments, the device may have radio-opaque markers to assist in correct positioning of the device.

Figure 7:
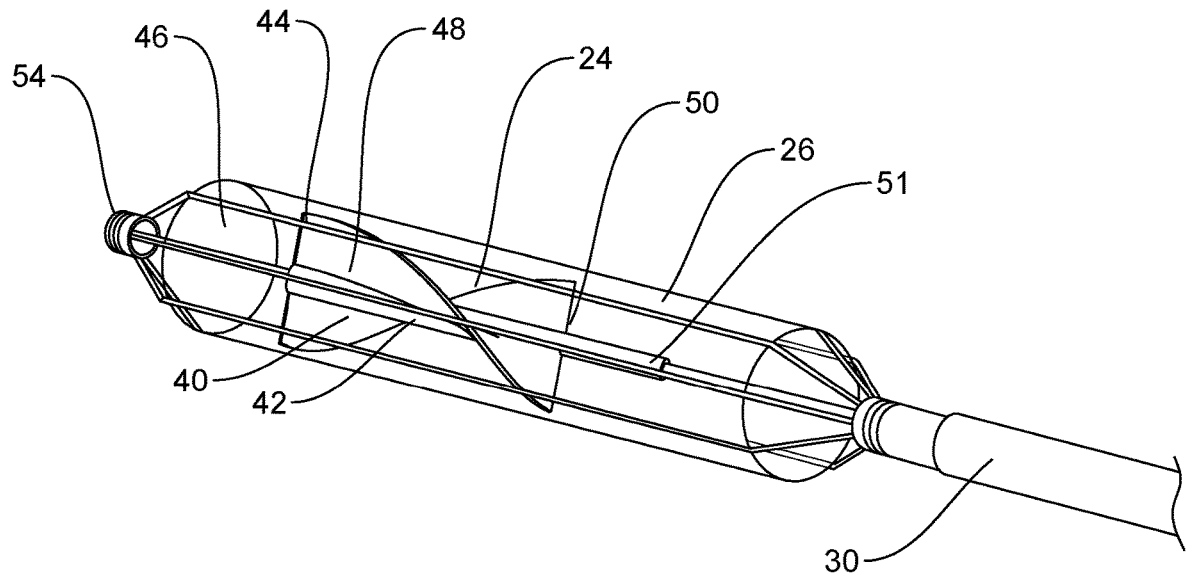
FIG. 7. is a perspective cross-sectional view of the impeller and the impeller cage in connection with the housing of the drive means.
Figure 8:
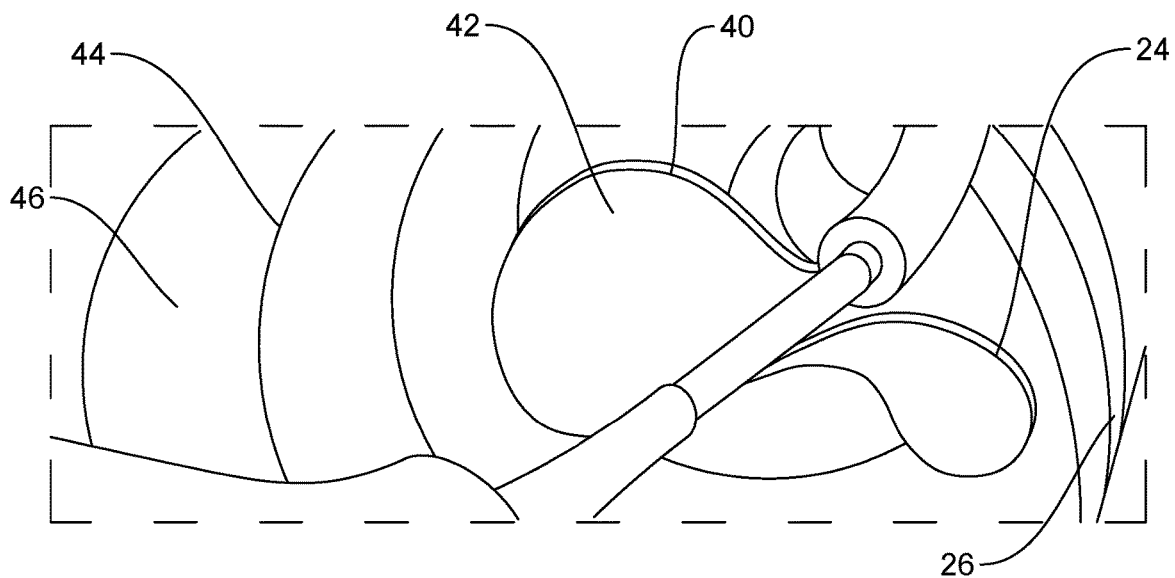
FIG. 8. is a perspective view of the impeller in the impeller cage.
Figure 14:
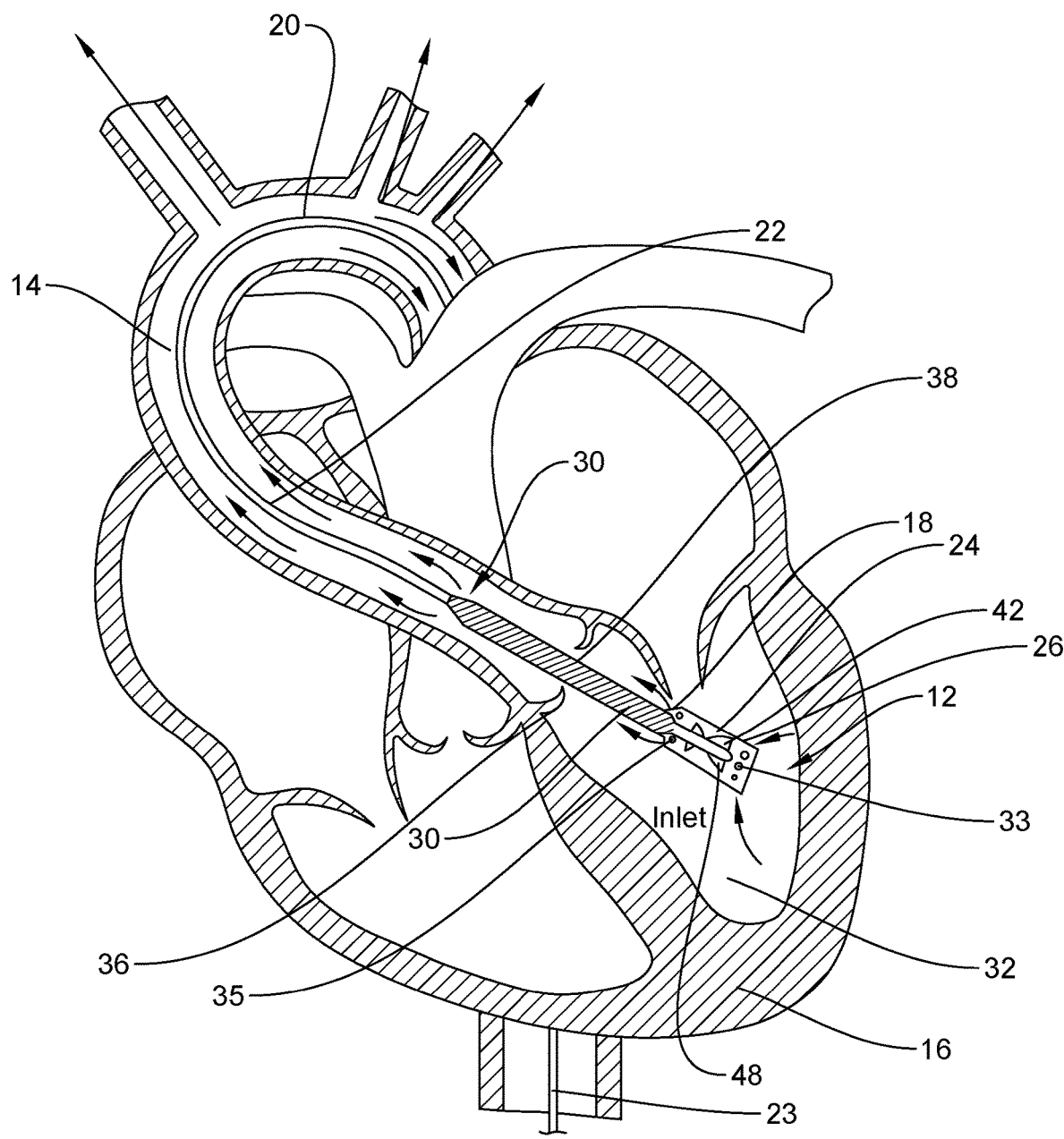
FIG. 14. is a cross-sectional schematic view of the impeller drive system with an internal motor embodiment of the present disclosure.

In an embodiment of the present invention, as illustrated in FIG. 14, shows a device 10 adapted for use in assisting blood flow from the left ventricle 12 to the aorta 14 of the heart 16 according to a preferred embodiment of the present invention. The device 10 may comprise an implantable blood pump 18 which may be mounted on a catheter 20 at a first end 22. As shown in FIGS. 7 and 8, the implantable blood pump 18 may comprise an impeller 24 which may be mounted in an impeller cage 26, and a drive means 28 which may be mounted in a housing 30. Preferably, the impeller 24 may be collapsible; and preferably, the impeller cage 26 may also be collapsible. The drive means 28 may be a drive shaft or a motor that may be capable to drive the rotational movement of the impeller 24. The housing 30 of the drive means 28 may be in connection between the first end 22 of the catheter 20 and the impeller cage 26.

Figure 3:
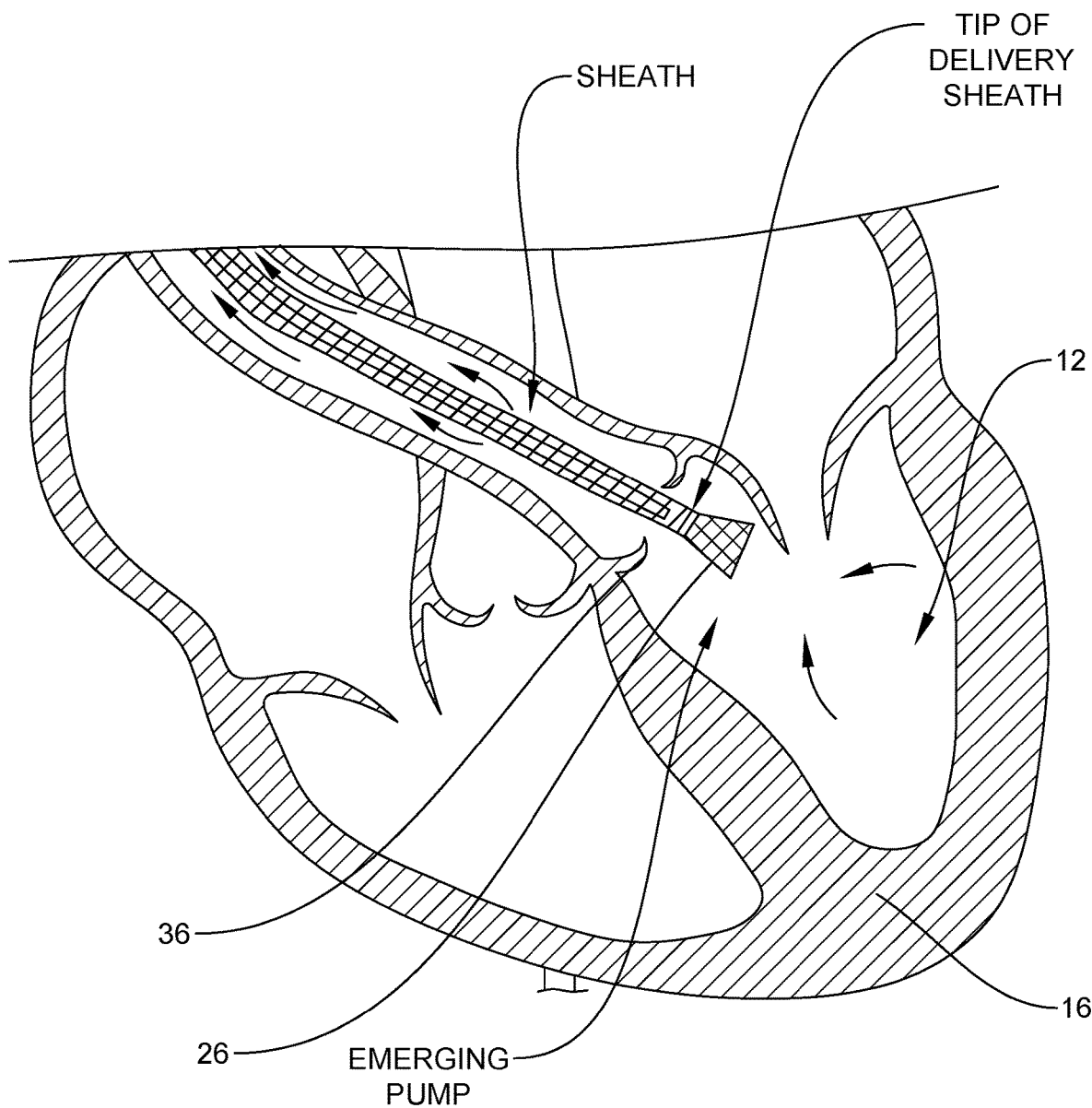
FIG. 3 is a cross-sectional schematic view of the deployment of the expandable version of the system in which a deployment sheath is being withdrawn allowing the pump to expand as it emerges from the sheath.

In operation, it is most preferable to insert the device into the patient with both the impeller 24 and the impeller cage 26 collapsed, as shown in FIG. 3. This is so that the device 10 may be navigated through the tortuous anatomy of the heart with reduced risk of snagging. Once the device 10 is located at the desired place of the patient's heart, such as when the implantable blood pump 18 is in the left ventricle 12, a retractable support structure 21 may be adapted to extend from the catheter 20. The extended retractable support structure 21 may be adapted to engage with the wall of the aorta 14 for allowing the implantable blood pump 18 to be secured in the left ventricle 12. The retractable support structure 21 may be at least one selected from the group of: a triangle stent-like structure or a diamond shaped structure (as shown in FIG. 4), a rounded stent-like structure (as shown in FIG. 5), a structs with barbs structure (as shown in FIG. 6), and any type of expanded mesh which can be adapted to securing the implantable blood pump 18 in the left ventricle 12. The implantable blood pump 18 may be adapted to be extendable along the longitudinal axis of the catheter away from the first end of the catheter 20. The collapsed impeller 24 and the collapsed impeller cage 26 may be expanded to a working configuration such that the impeller 24 is in the correct shape to operate and effect blood flow. The collapsible impeller cage 26 may comprise an inlet 32 or an inlet opening, and an outlet 34 or an outlet opening. In operation, the inlet 32 may allow for blood to flow into the expanded impeller cage when the impeller 24 is rotationally driven by a motor. In a preferred embodiment of the invention, the inlet 32 may be adapted to receiving blood from the left ventricle 12, and wherein the outlet 34 may direct blood in the direction of the atrioventricular valve 36. Preferably, the expanded impeller 24 and the expanded impeller cage 26 are in the left ventricle 12. Depending on how deep the expanded impeller cage 26 is in the left ventricle 12, the housing 30 or the catheter 20 may be through the atrioventricular valve 36. As depicted in FIG. 14, preferably the housing 30 may be through the atrioventricular valve 36. The outlet 34 may comprise a plurality of outlet apertures, wherein each of the outlet apertures may be relatively equidistant from each other. The housing 30 may comprise an outer Coanda surface 38 which may be adjacent to the outlet of the expanded impeller cage 26 such that blood is directed along the outer Coanda surface 38. The Coanda surface 38 may be used is so that the expelled blood stream or the outlet stream from the outlet 34 of the impeller cage 26 attaches to the curved surface and moving along the surface of the housing 30. The Coanda surface 38 may ensure that the expelled blood traverses along the surface of the housing 30 towards the atrioventricular valve 36. The force of the expelled blood stream may effect the opening of the atrioventricular valve 36, which then allows the blood stream to go from the left ventricle 12 to the aorta 14. It may be an advantage to expel the blood stream from the left ventricle 12 rather than in the aorta 14 such that atrioventricular valve 36 can be functionally openable to allow the periodic opening and closing of an atrioventricular valve 36 during a cardiac cycle. If the blood was expelled from the aorta 14, the atrioventricular valve 36 may not open at all which may be due to the pressure difference between the left ventricle and the aorta. It may therefore be a detriment to the patient's heart if the blood was expelled from the aorta 14.

Figure 9:
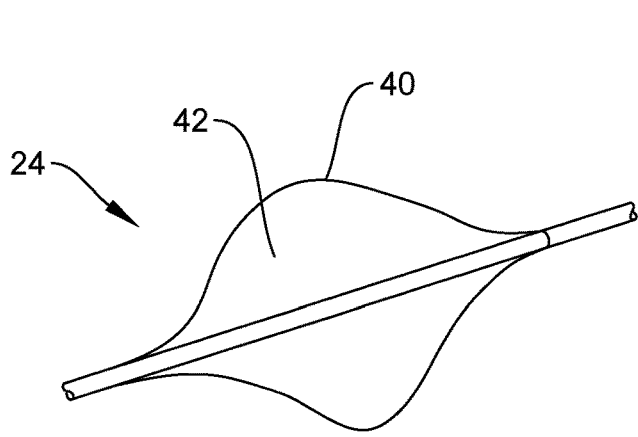
FIG. 9. is a perspective view of an impeller according to another embodiment of the present disclosure.
Figure 10:
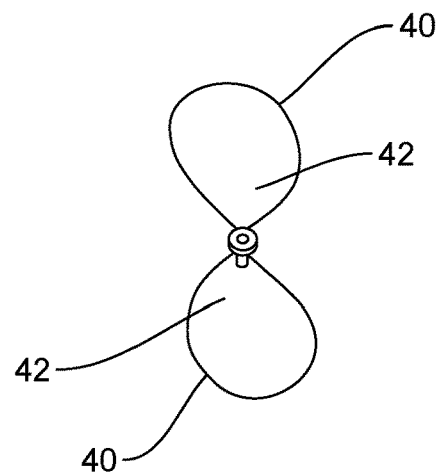
FIG. 10. is a an end view of the impeller of FIG. 9.

As shown in FIGS. 9 and 10, the collapsible impeller 24 may comprise a first metal 40 and a first membrane 42, the first membrane 42 may be in connection with the first metal 40, wherein the first metal 40 may define the blade frame of the collapsible impeller 24, and wherein the first membrane 42 may define the blade body of the collapsible impeller 24. Similarly, the collapsible impeller cage 26 may comprise a second metal 44 and a second membrane 46, the second membrane 46 may be in connection with the second metal 44, wherein the second metal 44 may define the frame of the collapsible impeller cage 26, and wherein the second membrane 46 may define the body of the collapsible impeller cage 26. Preferably, the first metal 40 and the second metal 44 are flexible; and preferably, the first membrane 42 and the second membrane 46 are also flexible. The material may be flexible such that the metal and the membrane may be able to collapse and expand back to shape suitable for operating. The material may be able to change between a compressed configuration and an expanded configuration, wherein the material may include a spring biasing means that may allow the material to convert from the compressed configuration to an expanded configuration when deployed or released by a release mechanism or arm (not shown).

The first metal may be a first shape-memory alloy, such as nitinol, and the second metal may be a second shape-memory alloy, which may also be nitinol as well. It may be appreciated that any type of shape-memory alloy can be used so that the impeller 24 and the impeller cage 26 can reform back to its desired shape from a collapsed configuration. The desired shape of the impeller cage 26 may be a cylindro-biconical shape as shown in FIG. 7. It may be appreciated that the desired shape may be any shape suitable to house the impeller 24 entirely when the impeller 24 is rotating or not rotating. The impeller cage 26 may protect the heart from the fast rotating impeller when in operation.

The first membrane 42 and the second membrane 46 may be a polymer. The polymer may be polyurethane, expanded polytetrafluoroethylene (ePTFE) or an elastomeric polymer so that it can also reform back to its desired shaped from a collapsed configuration. The elastomeric polymer may be at least one selected from the group of: Hapflex™ 598, Hapfex™ 798, Steralloy™, and Thoralon™. It may be appreciated that any type of elastomeric polymer with similar elasticity and property to the polymers listed in the group may be suitable for use.

The housing 30 of the drive means 28 may comprise a heat sink such that any heat generation from the moving parts within the housing may be able to dissipate and may minimise heating of the blood as the blood contacts and traverses over the surface of the housing 30. The moving parts within the housing may be the rotational movement of the cable for an external motor embodiment or the rotational movement of the internal motor for an internal motor embodiment. It may be not preferable to have the blood cool the housing of the drive means as the blood may heat up above the body system's optimal blood temperature.

Figure 11:
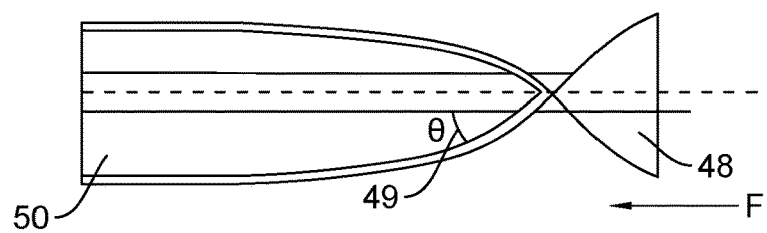
FIG. 11. is a side view of an impeller according to another embodiment of the present disclosure.
Figure 12:
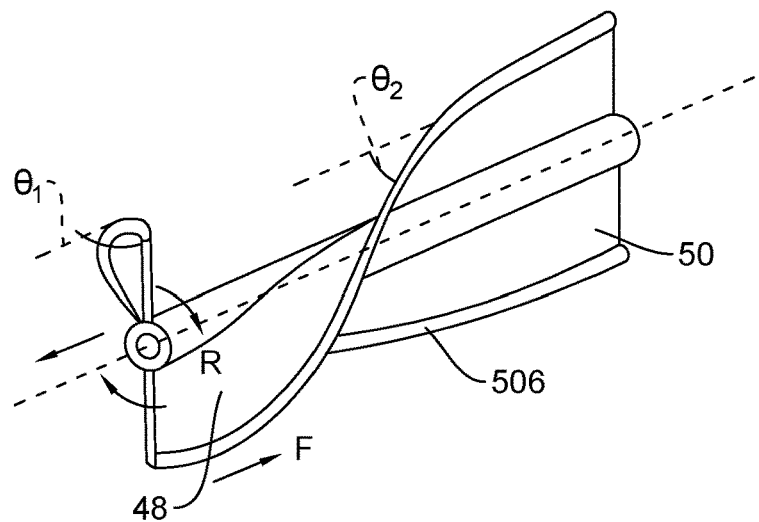
FIG. 12. is a perspective view of the impeller of FIG. 11.

As shown in FIGS. 11, 12 and 14, the collapsible impeller 24 may comprise a head portion 48 or a front portion and a tail portion 50 or a rear portion. In the expanded configuration, the impeller 24 may have an angle of attack 49 proximal to the head portion 48 compared to the tail portion 50. The head portion 48 is closest to the inlet 32 of the expanded impeller cage 26, while the tail portion 50 is closest to the outlet 34 of the expanded impeller cage 26. The support structure may be covered with a membrane which may provide for a flow straightener or alternatively the flow straightener could be built into the housing. In operation, as the expanded impeller 24 rotates, the blood may flow through the inlet 32 and into the expanded impeller cage 26. Once the blood may be in expanded impeller cage 26, the blood may contact the head portion 48 of the impeller 24 and the blood may spiral towards the tail portion 50 of the impeller 24. Spiral motion or a corkscrew movement of blood may lack directional precision as the blood exits the impeller cage 26. The spiral motion of the blood may then be straightened by the at least one flow straightener so that the blood flow is directed straight towards the direction of the housing 30 and to the catheter 20. The flow straightener may return the rotational energy of the fluid or blood with pressure energy as it straightens the blood flow.

The impeller cage 26 may comprise a plurality of inlet apertures for allowing blood to flow into the impeller cage 26. The plurality of inlet apertures may be located between a distal end of the impeller cage 26 and the head portion of the impeller 48. It may be an advantage to position the plurality of inlet apertures between the distal end of the impeller cage and the head portion so that the blood will flow from the inlet of the impeller cage to the head portion 48. The outlet of the impeller cage may comprise a plurality of outlet apertures, wherein each of the outlet apertures may be relatively equidistant from each other. A plurality of outlet apertures may be beneficial to allow multiple streams of expelled blood towards the housing 30 for a smoother flow rather than expelling from a bigger outlet aperture or opening.

Figure 15:
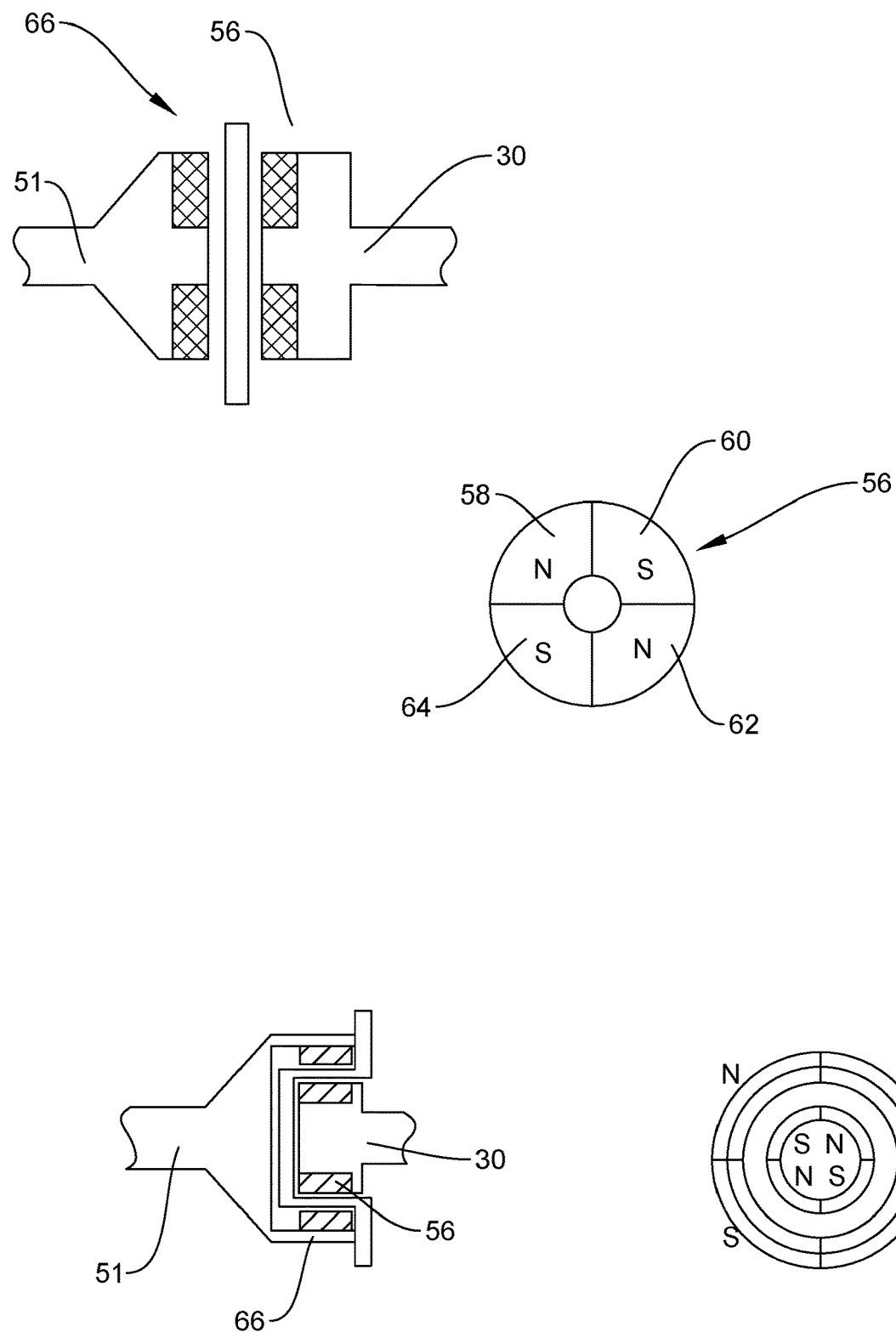
FIG. 15. is a cross-sectional schematic view of the drive means with a circular magnet embodiment of the present disclosure.

For driving the impeller 24, there may be a motor 55 adapted for providing rotational movement to the impeller 24. The motor 55 may be external to the patient or outside the body of the patient, in which case it may be referred to as the external motor 55. Or if the motor is internal to the patient or inside the body of the patient, in which case it may be referred to as the internal motor 55. For the external motor 55 embodiment of the present invention, the external motor 56 may be in communication with the second end of the catheter 23. The external motor 55 may comprise a magnet 56 mounted on an external motor 55. The magnet 56 may be circular, in which the magnet may have a first quadrant of a polarity 58 and the adjacent quadrants, such as the second quadrant 60 and fourth quadrant 64 may have the opposite polarity as shown in FIG. 15. The polarity of the third quadrant 62 may be the same as the polarity of the first quadrant 58. The magnet 56 of the motor 55 may interact with the magnet 68 of the cable in the catheter 20. It may be appreciated that the magnet 68 of the cable may be similar to the magnet 56 of the motor 55. The rotation of the magnet of the motor may then provide the rotational torque to the cable that may run through the catheter 20 which may then rotate the impeller 24 which may be located in the left ventricle 12. The external motor may be powered and controlled by the console 52. The external motor may be reuseable without the requirement of sterilising the external motor whereas for an internal motor embodiment, the motor is required to be sterilised before the device is safe and clean for use in patient. The catheter with drive cable and impeller or pump may be single use only. The external motor may be attached to the second end of the catheter and rotational torque may be transferred via magnetic coupling so that the external motor and the catheter drive cable do not require direct contact. It may be an advantage to reuse the external motor so as to reduce costs. Furthermore, having the external motor may not require any internal motors to be in the drive housing which may allow the diameter of the catheter to remain small which may be critical and key to device 10 with a collapsible pump or impeller. Small diameters may be advantageous for navigating through the tortuous anatomy of the heart to the left ventricle 12.

For the internal motor embodiment of the present invention, the internal motor may be in communication with the impeller 24. The internal motor 55 may comprise a magnet 56 mounted on an internal motor. The magnet 56 may be circular, in which the magnet may have a first quadrant of a polarity 58 and the adjacent quadrants, such as the second quadrant 60 and fourth quadrant 64 may have the opposite polarity to the first quadrant 58 as shown in FIG. 15. The polarity of the third quadrant 62 may be the same as the polarity of the first quadrant 58. The magnet 56 of the motor may interact with the magnet of the impeller axle 51 of the impeller 24. It may be appreciated that the magnet 66 of the impeller may be similar to the magnet 56 of the motor. The rotation of the magnet of the motor 56 may then provide the rotational torque to the impeller 24 which may be located in the left ventricle 12. The internal motor 55 may be powered by a power source, which may be a battery. The internal motor 55 may be controlled by the console 52. The internal motor may be small such as a micromotor which may be able to fit into the small diameter of the housing 30, the small size of which may be essential to navigate through the tortuous anatomy of the heart to the left ventricle 12.

For another internal motor embodiment of the present invention, as shown in FIG. 14, the internal motor may be attached to a drive shaft or a drive cable and may drive the drive shaft or drive cable. The drive shaft or drive cable may be connected to the impeller 24, in which the rotation of the drift shaft or drive cable by the internal motor may cause the impeller 24 to rotate. The internal motor 55 may be powered by a power source, which may be a battery. The internal motor 55 may be controlled by the console 52. The internal motor may be small such as a micromotor which may be able to fit into the small diameter of the housing 30.

Figure 13:
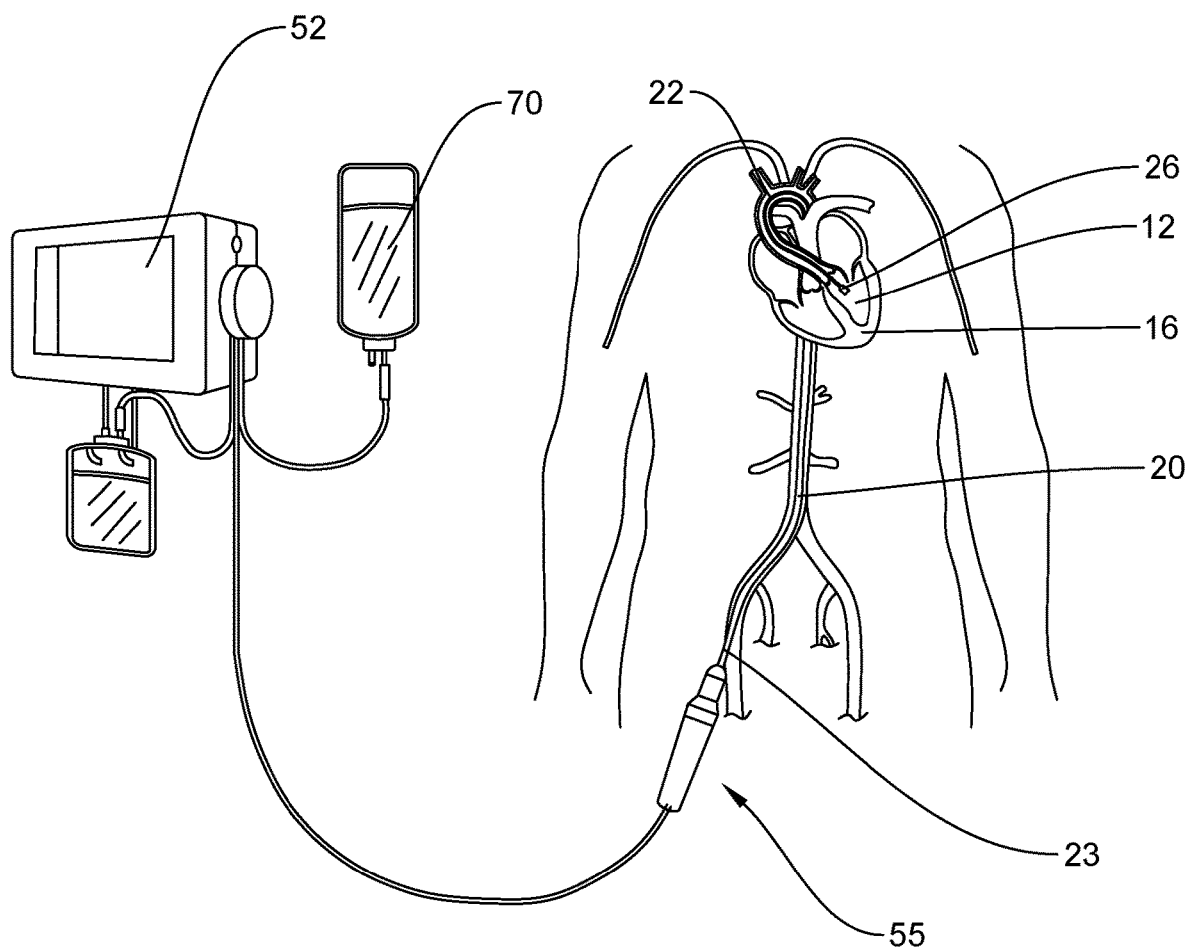
FIG. 13. is a cross-sectional schematic view of the impeller drive system with an external motor embodiment of the present disclosure.

As illustrated in FIG. 13, the console 52 may have an interface and controls to allow the professional to switch between the collapsed and expanded configuration of the device 10 into the patient. Further, the console 52 may allow the operation of the motor which in turn provide rotational torque to the expanded impeller or pump, when the device is at the desired location. For the external motor embodiment, the console 52 may be in electrical connection with external motor 55, in which the external motor 55 may be attachable to the second end 23 of the catheter 20, as illustrated in FIG. 15. For the internal motor embodiment, the console 52 may be in communication with the internal motor 55, in which the internal motor 55 may be able to effect rotational torque to the impeller 24. There may be a purge fluid 70, for example, saline or dextrose solution which may be pumped along the drive cable to lubricate and may prevent blood from getting into the catheter 20. Blood may clot around the seal and seals may not be 100% effective in which blood may still get through the seal and clot in the sheath. The purge fluid 70 may be injected along the catheter 20 and this may lubricate the rotating member or the impeller 24 and may be ejected into the blood flow. This may prevent any stagnant areas of blood where the rotating exists from the non-rotating sheath. As illustrated in FIG. 13, the bags or the containers containing the purge fluid 70 and the supply of the purge fluid may be regulated by the console 52 that may be external to the patient.

In another embodiment of the present invention, the system may have a rotating member which may be inside a non-rotating sheath, in which the sheath may be axially moved to start the expansion of the collapsed impeller 24 and the expansion of the collapsed impeller cage 26.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

The invention claimed is:

1. A device adapted for use in assisting blood flow from a left ventricle to an aorta of a patient heart, the device comprising:
    a catheter;
    an implantable blood pump located at a first end of the catheter;
    the implantable blood pump comprising a collapsible impeller mounted in a collapsible impeller cage; and
    a retractable support structure located on the catheter, wherein the retractable support structure is extendable to engage with a wall of the aorta to allow the implantable blood pump to be located in the left ventricle, wherein,
    the retractable support structure includes at least one of a triangular stent-like structure, a rounded stent-like structure, or an expanded mesh
    the collapsible impeller cage comprises an inlet and an outlet;
    the inlet is adapted to receive blood from the left ventricle; and
    the outlet directs blood toward an atrioventricular valve.

2. The device according to claim 1, wherein the collapsible impeller is expandable, wherein the collapsible impeller comprises a first metal and a first membrane, the first membrane is in connection with the first metal, wherein the first metal defines a blade frame of the collapsible impeller, and wherein the first membrane defines a blade body of the collapsible impeller.

3. The device according to claim 2, wherein collapsible impeller cage is expandable, wherein the collapsible impeller cage comprises a second metal and a second membrane, the second membrane is in connection with the second metal, wherein the second metal defines a frame of the collapsible impeller cage, and wherein the second membrane defines a body of the collapsible impeller cage.

4. The device of claim 3, wherein the first metal is a first shape-memory alloy, and wherein the second metal is a second shape-memory alloy.

5. The device of claim 3, wherein the first membrane and the second membrane is a polymer.

6. The device according to claim 1, wherein the collapsible impeller comprises a head portion and a tail portion, wherein an angle of attack is proximal to the head portion.

7. The device according to claim 1, wherein the inlet comprises a plurality of inlet apertures, wherein the plurality of inlet apertures is located between a distal end of the collapsible impeller cage and a head portion of the collapsible impeller.

8. The device according to claim 1, wherein the outlet comprises a plurality of outlet apertures, wherein each of the plurality of outlet apertures are relatively equidistant from each other.

9. The device of claim 1, wherein the retractable support structure includes a nitinol retractable support structure.

10. The device of claim 9, wherein the retractable support structure is the expandable mesh structure.

11. The device of claim 1, wherein the retractable support structure is the triangular stent-like structure.

12. The device of claim 1, wherein the retractable support structure is the rounded stent-like structure.

13. The device of claim 1, wherein the retractable support structure is covered with a membrane and configured as a flow straightener.

14. The device of claim 13, wherein the retractable support structure is the triangular stent-like structure.

15. The device of claim 13, wherein the retractable support structure is the rounded stent-like structure.

16. The device of claim 12, wherein the retractable support structure is the expandable mesh structure.

17. The device of claim 13, wherein the membrane is a polymer including at least one of polyurethane or other haemocompatible maternal.

* * * * *